United States Patent [19]

Benoist

[11] Patent Number: 5,741,251

[45] Date of Patent: Apr. 21, 1998

[54] DEVICE AND METHOD FOR REDUCING AND STABILIZING A BONE FRACTURE

[76] Inventor: Louis Benoist, 1400 Bellinger St., Eau Claire, Wis. 54703

[21] Appl. No.: 779,522

[22] Filed: Jan. 7, 1997

[51] Int. Cl.$^6$ ............................................. A61B 17/64
[52] U.S. Cl. ...................................... 606/54; 606/59
[58] Field of Search ............................. 606/54, 55, 56, 606/57, 58, 59, 69, 96

[56] References Cited

U.S. PATENT DOCUMENTS

| | | | |
|---|---|---|---|
| 4,554,915 | 11/1985 | Brumfield | 606/54 |
| 5,078,719 | 1/1992 | Schreiber | 606/87 |
| 5,250,048 | 10/1993 | Gundolf | 606/69 |
| 5,591,169 | 1/1997 | Benoist | 606/69 |

*Primary Examiner*—Michael Buiz
*Assistant Examiner*—David O. Reip
*Attorney, Agent, or Firm*—Breiner & Breiner

[57] ABSTRACT

A fixator for stabilizing bone fragments in a fractured radius bone comprising a template having at least three holes, and preferably at least six holes, positioned in the template for receiving wires which when passed through the holes and into bone fragments will hold the bone fragments in position in a preferred shape while the bone fragments are mending. The positioning of the holes in the template are designed in accordance with the golden ratio holding the bone fragments in a most pleasing shape while mending.

15 Claims, 3 Drawing Sheets

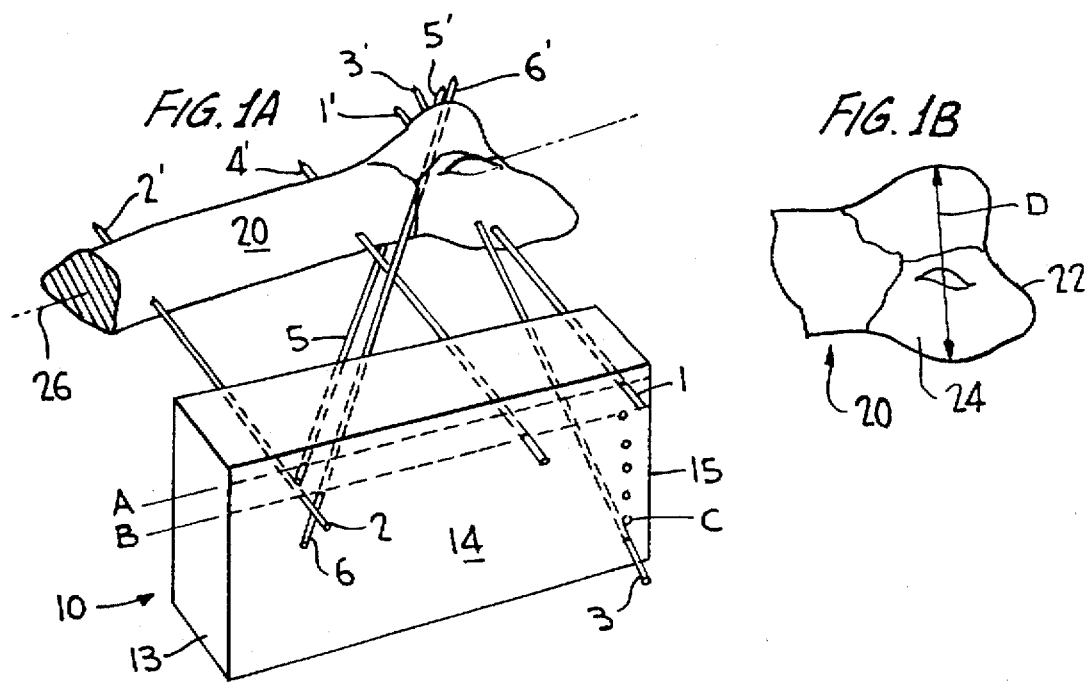
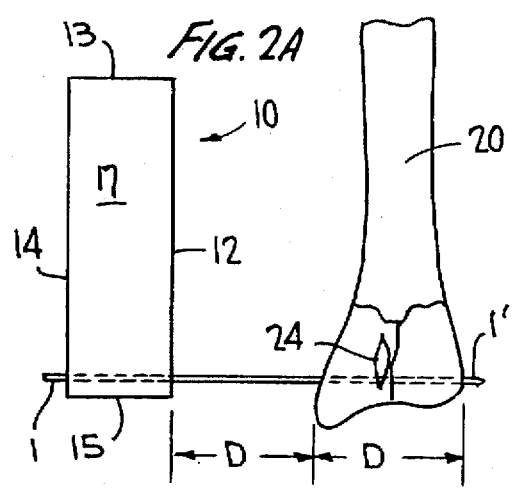
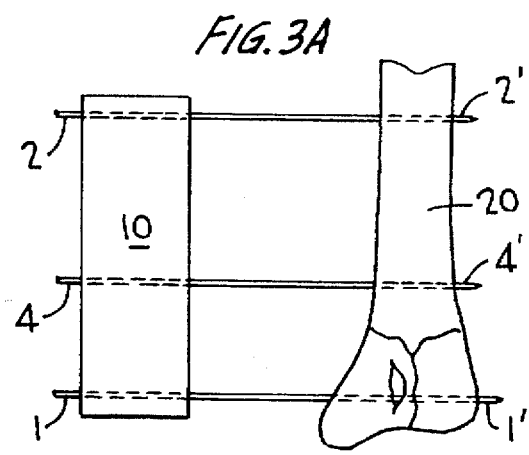
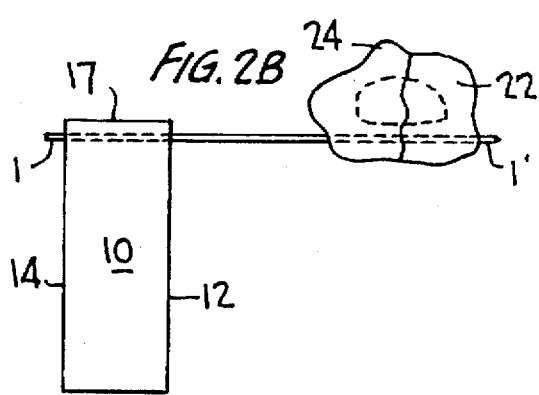
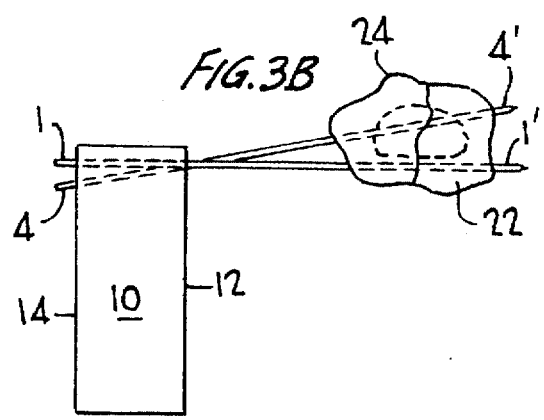

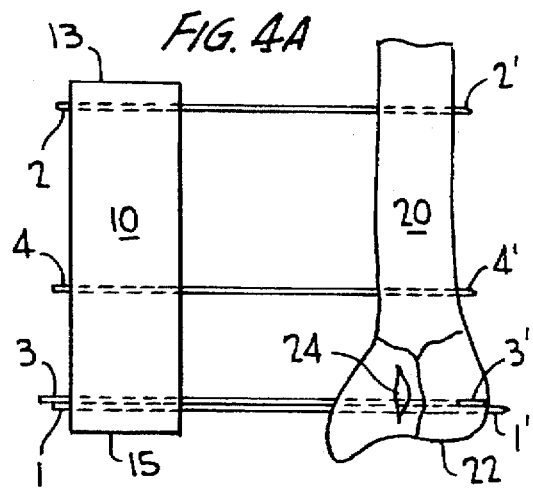
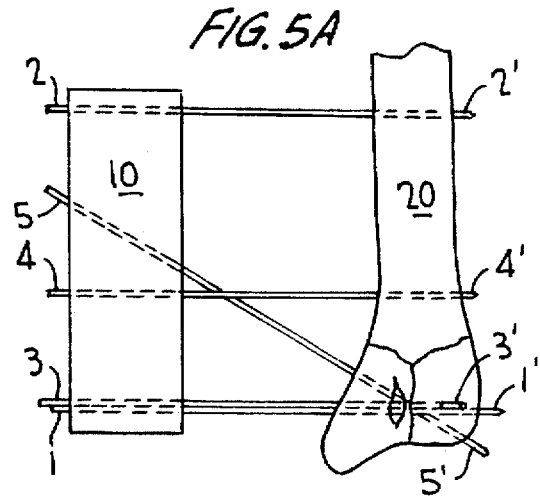
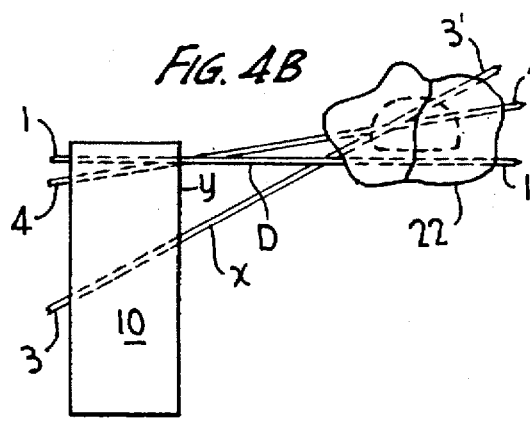
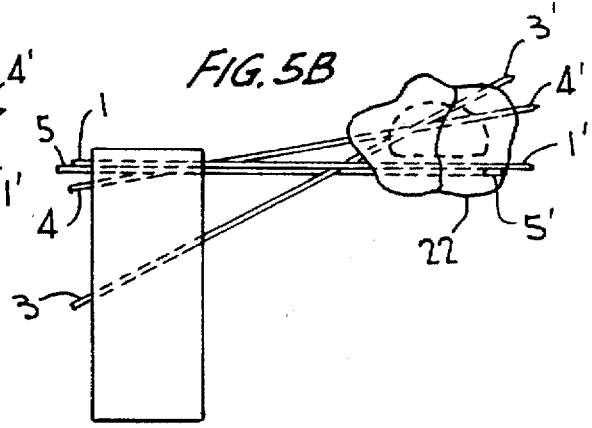
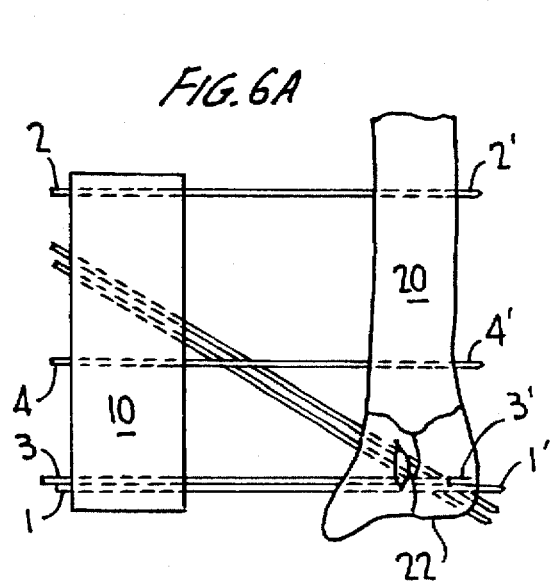
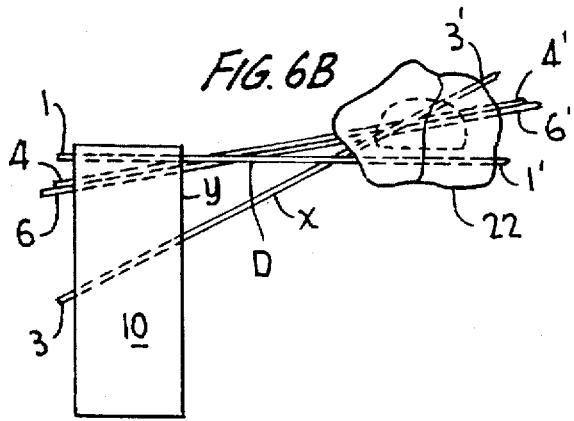

DEVICE AND METHOD FOR REDUCING AND STABILIZING A BONE FRACTURE

FIELD OF INVENTION

This invention relates to a method for reduction and fixation of a fractured wrist and to an external fixator for stabilizing the fracture while mending. The external fixator is positioned entirely on the radius bone and does not cross over to the hand, leaving the hand mobile.

BACKGROUND OF INVENTION

In a related application, U.S. Ser. No. 08/403,628 filed Mar. 14, 1995 entitled "Device And Method For Positioning And Holding Bone Fragments In Place," now U.S. Pat. No. 5,591,169, issued Jan. 7, 1997, the disclosure being incorporated herein by reference, there is described a template or bone organizer comprising a lightweight metal sheet, such as an aluminum sheet, having a plurality of holes. Preferably, the device will have an arcuate shape produced by taking a square piece of thin metal sheeting having a plurality of randomly placed holes and forming it into a series of corrugations. The device can be used to receive a plurality of positioning wires, commonly referred to as K-wires, positioned in the bone fracture in a number of different planes by adjusting and shaping the corrugated portion of the device to receive and accommodate the wires. Once the wires are inserted into the holes of the template or the bone organizer, the ends of the wires are held firmly in place using a fastener, such as a grommet, or with an adhesive cement. The template and wires are left in place while the fracture mends and thereafter removed and discarded.

Although the device described in the aforesaid application has substantial utility, there is still a need for a simplified device which provides a high degree of stability in holding mending fractured wrist bones in an ideal position.

SUMMARY OF INVENTION

The external fixator of the present invention is based on the theory that the most pleasing shape corresponds to the golden ratio of 1.618. Thus, the geometry of an unfractured wrist bone follows the golden ratio of 1.618 and, accordingly, is a "gnomon." When fracture of the wrist bone occurs, this golden ratio is distorted. When reducing the fracture, a primary objective is to recapture the golden ratio as seen in nature. According to the present invention, a block or template having a plurality of critically located holes for receiving wires which are inserted into bone fragments, commonly called K-wires, is provided for holding in place fragments of the fractured wrist for stabilization during mending. The location of the holes in the block and the location of wires in the block and bone fragments is based on the golden ratio of 1.618. Thus, a fixator block is provided wherein at least four pin holes for receiving wires or pins are located in the block so that after passing through the block the pins are critically positioned within bone fragments of the fracture for stabilization.

Specifically, a number 1 pin is passed through a hole in the block at one extreme end of the block and adjacent to the top of the block and into the radius bone at a critical location in the radius bone. Thus, the number 1 pin passes through the point of intersection of the Volar line of Lewis and Lister's tubercle, i.e., on a line on the long axis of the radius bone and perpendicular from Lister's tubercle. It is critical that this number 1 pin be maintained at this point so as to, inter alia, avoid passing through the rotary cavity of the radius bone.

The length "D" of the short axis of the radius bone is used to determine the distance between the exiting point of the pin from the block and the entrance into the radius bone. This pin is then fixed within the block and forms the basis for inserting additional pins.

Pin number 2 is passed through a second hole in the block and into the radius bone. This pin number 2 passes through the block at an angle to a point on the radius bone above the Volar line of Lewis. The site of the pin has to be "Out of Length," i.e., reduces the fracture as to the long axis of the fracture. Specifically, the positioning of the pin in the block will be at an angle of 8 to 14 degrees relative to the top of the block, when the block is maintained directly parallel to the line of Lewis of the radius bone, and will enter the radius bone above the line of Lewis. The positioning of this pin prevents impaction of the bone fragments, as well as disfraction and serves as an angular guide.

Pin number 3 passes through a hole in the block at the same extreme end of the block as pin number 1, but at an angle so as to enter the radius bone at substantially the same point as pin number 1. Pin numbers 1 and 3 form an apex at their point of entry into the radius bone and form a 30 degree angle relative to the radius bone. Accordingly, the length of the portion of pin number 3 between the face of the block and the bone will be substantially length "D." More specifically, length $x=\sqrt{D^2+Y^2}$, Y being the length along the face of the block. The positioning of this pin is critical and is again based on the golden ratio of 1.618 being maintained by anatomic reduction. The angle can vary at most one or two degrees off the 30 degree angle.

A fourth pin on substantially the same plane as pin number 2, which can be inserted before or after pin number 3, enters the radius bone behind (proximate to) the fracture and before pin number 2 and is substantially on the same plane as pin number 2. This pin holds the radius bone in line so as to prevent a downward sagging of the fracture in the metaphyseal area.

Optionally, additional pins 5 and 6 can be inserted to further stabilize the fracture while mending. Pin number 5, if used, will be on substantially the same line as pin number 1 but will enter the bone fracture at an angle so as to exit the fracture at substantially the same position as pin numbers 1 and 3. The angle of pin numbers 1 and 5 will be approximately 30 degrees. Similarly, if pin number 6 is utilized, it will pass through a hole in the block at an angle of approximately 8 to 14 degrees tilt, similar to pins 2 and 4, and enter the fracture so as to exit the fracture substantially at the same point as pin number 1. Thus, pin numbers 3 and 6 form an apex and pin numbers 1 and 5 form an apex.

Additional pins can be utilized, if desired, to provide further stability but such additional pins are normally unnecessary.

As above stated, the location of the holes in the block and location of the pins in the radius bone are designed based on the golden radio and in that sense are critical within the aforesaid tolerances.

In the method of using the bone fixator, the doctor will first reduce the fractured bone so as to reconstitute the most pleasing shape (anatomic reduction). This requires, therefore, the reduction of the bone fracture in the long and short axis of the bone and thereafter the insertion of the various pins as above described always maintaining fracture reduction. Thus, according to the method of the invention as described in U.S. Pat. No. 5,591,169, the bone pieces of the fractured wrist are reduced to the most pleasing shape. Thereafter, the first pin is inserted into the bone pieces and then fixed in a critical position relative to the template block. Thereafter, the additional pins are inserted to hold the radius bone including the fragments of the fracture in a critical position by anchoring the wires into the template block and fixing the ends of the wires to the template block.

THE DRAWING AND DETAILED DESCRIPTION

FIG. 1A illustrates a template block positioned parallel to the Volar line of Lewis of a fractured radius bone with fixator pins 1–6 positioned in the radius bone stabilizing the fracture in the template block;

FIG. 1B is a plan view of the end of a fractured radius bone with the bone fragments reduced to the most pleasing shape;

FIG. 2A is a plan view of the template block parallel to the Volar line of Lewis of a fractured radius bone with pin number 1 inserted through the template block and through the extreme end of the fractured radius bone;

FIG. 2B is the end view of the illustration of FIG. 2A;

FIG. 3A is a plan view similar to the plan view of FIG. 2A except that pins 2 and 4 are positioned in the template block and in the radius bone;

FIG. 3B is an end view of the illustration of FIG. 3A;

FIG. 4A is a view similar to FIG. 3A except that pin 3 is properly positioned through the template block and into the radius bone;

FIG. 4B is an end view of the illustration of FIG. 4A;

FIG. 5A is a view similar to FIG. 4A except that pin 5 is positioned in the template block and through the radius bone;

FIG. 5B is an end view of the illustration of FIG. 5A;

FIG. 6A is a view similar to FIG. 5A except that pin 6 is positioned in the template block and through the radius bone;

FIG. 6B is an end view of the illustration bone in FIG. 6A;

Figure 7:
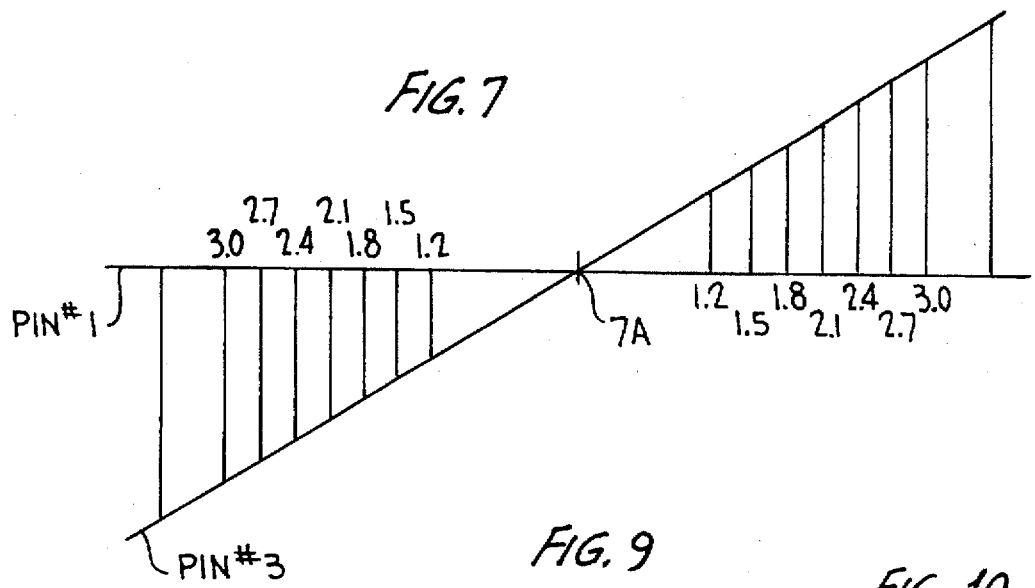
FIG. 7 is a plan diagrammatic view of a template for conveniently measuring distances from radial insertional site and radial side of template block.
Figure 8:
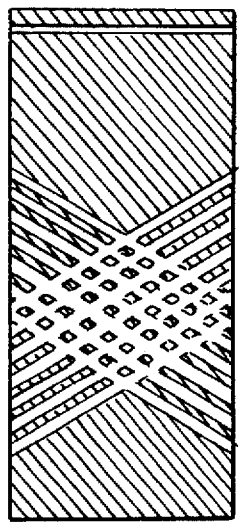
Figure 9:
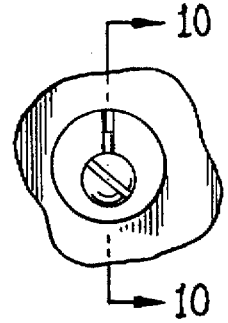
Figure 10:
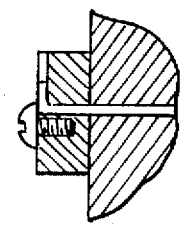

FIG. 8 is a sectional view through the end of the template block showing therein the hole for positioning pin 1 and a plurality of holes 3 for selectively positioning pin 3;

FIG. 9 is a plan view of a grommet for holding pins 1–6 in position in the template;

FIG. 10 is a cross sectional view of the illustration of FIG. 9, and

Figure 11:
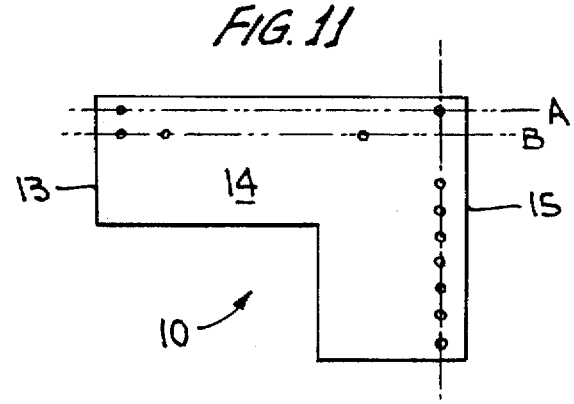

FIG. 11 is a side view of the template block constructed in the shape of a lazy "L."

Referring to the drawings, as best shown in FIGS. 1, 2A, and 11, template block 10 has sides 12 and 14 and ends 13 and 15. As shown, the block has a first row of holes A extended in a horizontal line adjacent the top 17 of block 10. The holes in row A extend from surface 14 to surface 12 of the block. The hole for receiving pin number 1 passes straight through the block whereas the hole for receiving pin number 5 passes through the block at an angle. Thus, these holes extend through from side 14 closer to end 13 exit at surface 12 closer to end 15.

A second row of holes B, extending in a horizontal line below the holes of row A, pass through the block at an angle so that the holes exit from the surface 12 of the block adjacent top 17. The angle of these holes from entrance to exit is from about 8°–14°.

Additionally, there is a third row of holes C positioned in a vertical line adjacent end 15 extending from surface 14 to surface 12 at an angle of 30° plus or minus 2°. As shown in FIG. 8, the plurality of holes in line C can extend in rows crossing each other. This is so that the template block can be used to fixate or stabilize either a right or left radius bone. Similarly, the rows of holes A and B will be similarly positioned in the block for stabilizing either a right or left radius bone. Thus, the block is designed so that holes can enter at either surface 12 or 14, depending upon whether the fracture is in a right or left radius bone.

Referring to FIG. 1B, there is shown the end of a fractured radius bone with that fracture properly reduced in accordance with its most pleasing shape based on the golden ratio. FIG. 1B illustrates Lister's tubercle at 24 and shows the shape of end 22 of the radius bone.

In FIG. 1A a template block 10 is positioned parallel to the Volar line of Lewis of radius bone 20. As shown, pins 1–6 each pass through template block 10 and then into and through radius bone 20 and exit therefrom at points 1' through 6'. The positioning of the pins through the block is designed to fixate and stabilize the fracture without crossing the wrist. As such, the hand during the mending of the fracture is completely mobile.

Now referring to FIGS. 2A through 6A, a more detailed description of the insertion of pins 1–6 and the reason therefore will be set forth.

FIG. 2A is a plan view showing template block 10 positioned parallel to the Volar line of Lewis of radius bone 20 and positioned away from the radius bone by a distance D which is the length D of the end 22 of radius bone 20 at the level of Lister's tubercle as shown in FIGS. 1B and 2A. This distance is critical to the extent that the distance D between template block 10 and radius bone 20 cannot vary from the length of the end of the radius bone by more than about 1–2 mm. As illustrated in FIGS. 2A and 2B, pin 1 passes through block 10 on a straight line and into the fractured radius bone 20 on a straight line. It is essential, as shown in FIG. 2A, that pin 1 passes adjacent the end of Lister's tubercle to ensure that the pin does not cross the rotary cavity of end bone 22 and thus interfere with the rotation of the forearm.

FIGS. 3A and 3B illustrate the positioning of pins 2 and 4. As shown in plan view 3A, the pins pass through block 10 and into radius bone 20 and exit from the radius bone at points 2' and 4'. As shown in FIG. 3B, pins 2 and 4 are on the same plane with pin 4 being forward (distal), i.e., toward pin 1, of pin 2 and, accordingly, not seen in end view 3B. As shown in 3B, however, pin 4 passes through block 10 at a tilt or angle and thus, into radius bone 20 at an angle. This tilt can vary from about 8° to 14°. It is desired that pins 2 and 4 enter the radius bone above the level of the top of block 10 to spare the Volar cortex of the radius. Pin 2 holds the reduced fracture "Out of Length" which means it holds the fracture as to the long axis of the fracture thus preventing compaction. Pin 4 holds the fractured bone so as to prevent sagging of the fracture site.

FIGS. 4A and 4B illustrate the entrance and positioning of pin 3. The positioning of this pin is particularly critical and it must pass through the block 10 so that pins 1 and 3 are at and angle of about 30° plus or minus 2°. This ensures that the pins enter the radius bone at substantially the level of Lister's tubercle on the Volar line of Lewis as does pin number 1. As will be apparent, the angle at point of entrance and the angle at point of exit is substantially the same angle which will be determinable by using template 7 so that the template at point 7A is at the point of entrance of pins 1 and 3 of the radius bone. This provides for a exceptional pleasing fixation and stabilization of the fragments of the fractured bone.

As illustrated in FIGS. 5A and 5B, pin 5 can be utilized to improve the stabilization of the fracture. As best illustrated in FIG. 5A, pin 5 passes through block 10 at an angle and enters the radius bone 20 at an angle and passes under pins 3 and 5 substantially on line with Lister's tubercle. Again this positioning is critical to prevent interference by pin 5 in the rotary cavity of end 22 of the radius bone. As shown in FIG. 5B, pin 5 passes through block 10 in a line and enters the radius bone in a line parallel to the Volar line of Lewis of the radius bone.

As illustrated in FIGS. 6A and 6B, if desired a sixth pin can be utilized which passes through block 10 at a tilt so that it enters the radius bone at a level lower than the level that it passes out of the radius bone and thus makes an apex at pin tip of pin number 3 in the posteromediol area.

The positioning of the pins in the template block 10 and relative to the radius bone 20 is designed to provide an accurate fixation of the reduced bone so as to hold the reduced bone in its most pleasing shape during the mending of the bone. As a result of the fixation and stabilization, there is no difficulty in rotation of the radius bone relative to the hand when mending is complete and when the fixator is removed.

As shown in FIGS. 9 and 10, pins 1–6 are locked in place in the template block 10 using a grommet member which fixes the end pins at surface 14 of the block. These grommets are fully described in U.S. Pat. No. 5,591,169, the disclosure being incorporated by reference.

As will be apparent to one skilled in the art, various modifications can be made within the scope of the aforesaid description of the novel template and method of stabilizing a fractured radius bone, such modifications being within the ability of one skilled in the art form a part of the present invention and are embraced by the appended claims.

It is claimed:

1. A fixator for stabilizing bone fragments in a fractured radius bone comprising a block template, said template having a top, a first end, a second end, a first side and a second side, said template having a plurality of holes extending from said first side to said second side, each of said plurality of holes being sized to receive a wire for insertion, after being passed from said first side to said second side of said template, into bone fragments with the plurality of holes being located in said template as follows:

a first hole adjacent to the top and a first end of said template, said first hole extending from said first side through said template in a straight line to exit at said second side;

a second hole spaced at a level below said first hole in said template and spaced toward said second end of said template, said second hole extending through said template at an upward angle whereby said hole enters the first side of said block at a first level and exits from the second side of said template at a second level higher than said first level;

a third hole adjacent to said first end of said template and spaced below and in line with said first hole and passing through said template at a 30° angle ±2° whereby a wire passing through said first hole and a wire passing through said third hole forms a 30° plus or minus 2° angle, said template constructed and arranged in order that wires passing through said plurality of holes in said template and into fragments of a fractured radius bone, holds said fractured radius bone in a desired shape while mending.

2. The fixator of claim 1 wherein said first hole is one of a plurality of holes in a first line, with said plurality of holes in said line passing through said template from the first side to said second side; said second hole is one hole in a second line of holes, said second line being positioned below said first line and extending through said template from said first side to said second side at an upward angle, and said third hole is in a line of holes extending from top to bottom of said template, said holes passing through said template at an upward angle of 30° plus or minus 2°.

3. The fixator of claim 2 wherein said template is configured as a rectangular block.

4. The fixator of claim 2 wherein said template is configured as an L-shaped block.

5. The fixator of claim 3 or claim 4 wherein said upward angle is an angle from 8° to 14°.

6. The fixator of claim 3 or claim 4 wherein a fourth hole is in said first line with said fourth hole passing through said template on an angle from said first side to said second side of the said block.

7. The fixator of claim 6 wherein said angle of passage of said fourth hole is an angle of 30°±2°.

8. The fixator of claim 3 or claim 4 wherein a fifth hole passes through said template from said first side to said second side having the same upward angle as said second hole.

9. The fixator of claim 8 where there is a sixth hole in the second line with said sixth hole passing through said block at the same upward angle as the second and fifth holes and at a slant whereby the hole enters the first side at a point closer to said second end and exits at a point closer to said first end, said slant forming an angle through said template of from 30°±5°.

10. A method of reducing and stabilizing a fractured radius bone comprising the steps of:

a) reducing said bone fragments to a most pleasing shape based on the golden ratio of 1.618;

b) positioning a template having at least a first, second and third hole passing through said template substantially parallel to the Volar line of Lewis of said radius bone and at a distance equal to the thickness of the end of the radius bone ±1–2 mm;

c) passing a first wire through said first hole in said template whereby said first hole extends directly through said template and into fragments of said fractured radius bone at a point perpendicular to the Volar line of Lewis and at the level of Lister's tubercle;

d) passing a second wire through said template at an angle from a first side of said template through the second side of said template and into the radius bone at a point above the Volar line of Lewis;

e) passing a third wire from the first side of said template through to the second side of said template at an angle of 30°±2° and into said bone fragments, said third wire being directly below said first wire and said first and third wire forming an angle of 30°±2° at the point of entrance of said first and third wire into the fragments of said radius bone; and f) stabilizing said wires within said template whereby the fractured radius bone is stabilized in a most pleasing shape based on the golden ratio.

11. The method of claim 10 wherein a fourth wire is passed through the template block and into the radius bone above the radius bone at the same angle as said second wire but at a position closer to said first wire than said second wire.

12. The method of claim 11 wherein a fifth wire is passed through said template on the same line as said first wire but at a slant so that the exit of fifth wire is at a point closer to said first wire than its entrance and then into the radius bone substantially parallel to the Volar line of Lewis.

13. The method of claim 12 wherein a sixth wire is passed through said template at the same angle as said second and fourth wire but at a slant whereby said sixth wire exits the template at a point closer to said first wire than its entrance and then into said fractured radius bone at an angle and above the Volar line of Lewis.

14. The method of claim 12 wherein said first and fifth wire form an apex of 30°±2° within said radius bone.

15. The method of claim 13 wherein said third and sixth wires form an angle of 30°±2° at the apex of said wires.

* * * * *